(12) United States Patent
Nesbitt et al.

(10) Patent No.: US 7,993,135 B2
(45) Date of Patent: Aug. 9, 2011

(54) AIR POLISHING PROPHYLAXIS SYSTEM

(75) Inventors: Lanny Edward Nesbitt, Strasburg, PA (US); Matthew Van Barto, Dallastown, PA (US); Patrick Eugene Riley, Timontium, MD (US)

(73) Assignee: Dentsply International, Inc., York, PA (US)

( * ) Notice: Subject to any disclaimer, the term of this patent is extended or adjusted under 35 U.S.C. 154(b) by 1164 days.

(21) Appl. No.: 11/244,634

(22) Filed: Oct. 6, 2005

(65) Prior Publication Data

US 2006/0160046 A1 Jul. 20, 2006

Related U.S. Application Data

(60) Provisional application No. 60/618,801, filed on Oct. 14, 2004.

(51) Int. Cl.
*A61C 3/02* (2006.01)

(52) U.S. Cl. ........................................ 433/88

(58) Field of Classification Search ............... 433/87, 433/88, 82, 216, 80, 81, 83–86, 89, 90; 222/630, 222/631, 93–96, 153.11, 209, 373, 389, 394; 604/19, 27, 131, 140, 147, 151
See application file for complete search history.

(56) References Cited

U.S. PATENT DOCUMENTS

| | | | |
|---|---|---|---|
| 2,759,266 A * | 8/1956 | Cassani | 433/88 |
| 3,698,088 A | 10/1972 | Austin, Jr. | |
| 3,955,284 A | 5/1976 | Balson | |
| 3,977,084 A | 8/1976 | Sloan | |
| 3,990,452 A | 11/1976 | Murry et al. | |
| 4,026,025 A | 5/1977 | Hunt | |
| 4,174,571 A * | 11/1979 | Gallant | 433/216 |
| 4,248,589 A | 2/1981 | Lewis | |
| 4,251,212 A | 2/1981 | Worschischek et al. | |
| 4,278,428 A | 7/1981 | Straihammer et al. | |
| 4,279,596 A | 7/1981 | Weber | |
| 4,439,966 A | 4/1984 | Alles | |
| 4,462,803 A | 7/1984 | Landgraf et al. | |
| 4,485,303 A | 11/1984 | Suzuki | |
| 4,486,175 A | 12/1984 | Fisher et al. | |
| 4,561,431 A | 12/1985 | Atkinson | |
| 4,582,060 A | 4/1986 | Bailey | |
| 4,595,365 A | 6/1986 | Edel et al. | |

(Continued)

FOREIGN PATENT DOCUMENTS

EP 0 454 672 1/1996

(Continued)

*Primary Examiner* — Cris L Rodriguez
*Assistant Examiner* — Sunil K Singh
(74) *Attorney, Agent, or Firm* — Douglas J. Hura; Leana Levin; David A. Zdurne

(57) ABSTRACT

A dental apparatus provides a substantially uniform concentration of abrasive material entrained in a pressurized gas to a desired location substantially irrespective the amount of abrasive material in a pressurized container of the apparatus, and resists clogging by the abrasive material. The apparatus includes a control unit having a container that secures the abrasive material, the abrasive material in the container becoming entrained in pressurized gas received from a dental unit. The concentration of the mixture of entrained abrasive material in pressurized gas is maintained by upwardly directing the flow of the mixture in a first conduit against a cap, a portion of the entrained abrasive material returning to the container, with the regulated mixture of entrained abrasive material in pressurized gas being delivered through a hand piece to the desired location.

25 Claims, 6 Drawing Sheets

U.S. PATENT DOCUMENTS

| | | |
|---|---|---|
| 4,604,058 A | 8/1986 | Fisher et al. |
| 4,655,197 A | 4/1987 | Atkinson |
| 4,675,004 A | 6/1987 | Hadford et al. |
| 4,676,749 A | 6/1987 | Mabille |
| 4,696,645 A | 9/1987 | Saupe et al. |
| 4,712,813 A | 12/1987 | Passerell et al. |
| 4,795,343 A | 1/1989 | Choisser |
| 4,872,837 A | 10/1989 | Issalene et al. |
| 4,900,068 A | 2/1990 | Law |
| 4,907,968 A | 3/1990 | Eisner et al. |
| 4,973,248 A | 11/1990 | Sigler |
| 4,975,054 A | 12/1990 | Esrock |
| 4,978,297 A | 12/1990 | Vlock |
| 4,984,984 A | 1/1991 | Esrock |
| 4,998,880 A | 3/1991 | Nerli |
| 5,046,486 A | 9/1991 | Grulke et al. |
| 5,049,071 A | 9/1991 | Davis et al. |
| 5,067,899 A | 11/1991 | Paschal |
| 5,090,904 A | 2/1992 | Bailey |
| 5,094,615 A | 3/1992 | Bailey |
| 5,100,319 A | 3/1992 | Baum |
| 5,125,835 A | 6/1992 | Young |
| 5,186,625 A | 2/1993 | Bailey |
| 5,192,206 A | 3/1993 | Davis et al. |
| 5,203,697 A | 4/1993 | Malmin |
| 5,203,698 A | 4/1993 | Blake et al. |
| 5,232,362 A | 8/1993 | Kanas |
| 5,236,356 A | 8/1993 | Davis et al. |
| 5,242,300 A | 9/1993 | Esrock |
| 5,286,065 A | 2/1994 | Austin et al. |
| 5,295,827 A | 3/1994 | Fundingsland et al. |
| 5,306,146 A | 4/1994 | Davis et al. |
| 5,330,354 A * | 7/1994 | Gallant .................. 433/88 |
| 5,334,019 A | 8/1994 | Goldsmith et al. |
| 5,336,089 A | 8/1994 | Sakurai |
| 5,336,202 A | 8/1994 | Bailly et al. |
| 5,340,311 A | 8/1994 | Sakurai |
| 5,342,195 A | 8/1994 | Davis et al. |
| 5,350,299 A | 9/1994 | Gallant |
| 5,356,292 A | 10/1994 | Ho |
| D352,354 S | 11/1994 | Davis et al. |
| 5,376,003 A | 12/1994 | Rizkalla |
| 5,378,149 A | 1/1995 | Stropko |
| 5,401,249 A | 3/1995 | Shields |
| 5,433,485 A | 7/1995 | Austin, Jr. et al. |
| 5,460,619 A | 10/1995 | Esrock |
| 5,468,027 A | 11/1995 | Guest |
| 5,468,148 A | 11/1995 | Ricks |
| 5,474,450 A | 12/1995 | Chronister |
| 5,489,205 A | 2/1996 | Davis et al. |
| 5,490,779 A | 2/1996 | Malmin |
| 5,525,058 A | 6/1996 | Gallant et al. |
| 5,538,425 A | 7/1996 | Reeves et al. |
| 5,540,587 A | 7/1996 | Malmin |
| 5,547,376 A | 8/1996 | Harrel |
| 5,554,026 A | 9/1996 | Van Hale |
| 5,591,389 A | 1/1997 | Esrock |
| 5,593,304 A | 1/1997 | Ram |
| 5,618,177 A | 4/1997 | Abbott |
| 5,647,746 A | 7/1997 | Chipman |
| 5,678,273 A | 10/1997 | Porcelli |
| 5,718,581 A | 2/1998 | Fernwood et al. |
| 5,725,370 A | 3/1998 | Himeno et al. |
| 5,746,596 A | 5/1998 | Gallant et al. |
| 5,752,829 A | 5/1998 | Goldsmith et al. |
| 5,765,759 A | 6/1998 | Bruns et al. |
| 5,772,433 A | 6/1998 | Esrock |
| 5,810,587 A * | 9/1998 | Bruns et al. ............ 433/88 |
| 5,833,456 A | 11/1998 | Davis et al. |
| 5,848,893 A | 12/1998 | Martin et al. |
| 5,857,851 A | 1/1999 | Chavanne |
| 5,868,563 A | 2/1999 | Davis et al. |
| 5,876,201 A | 3/1999 | Wilson et al. |
| 5,899,692 A | 5/1999 | Davis et al. |
| 5,899,693 A | 5/1999 | Himeno et al. |
| 5,908,296 A | 6/1999 | Kipke et al. |
| 5,927,976 A | 7/1999 | Wu |
| 5,941,702 A | 8/1999 | Sharp et al. |
| 5,944,521 A | 8/1999 | Lawler |
| 5,984,677 A | 11/1999 | Fernwood et al. |
| 5,997,518 A | 12/1999 | Laibovitz et al. |
| 6,048,200 A | 4/2000 | Martin et al. |
| 6,083,002 A | 7/2000 | Martin et al. |
| 6,093,020 A | 7/2000 | Pond et al. |
| 6,113,391 A | 9/2000 | Esrock |
| 6,142,170 A | 11/2000 | Belfer et al. |
| 6,149,429 A | 11/2000 | Bukowski et al. |
| 6,149,509 A | 11/2000 | Bruns et al. |
| 6,183,252 B1 | 2/2001 | Huang |
| 6,238,211 B1 | 5/2001 | Esrock |
| 6,247,929 B1 | 6/2001 | Bachman et al. |
| 6,250,921 B1 | 6/2001 | Esrock |
| RE37,324 E | 8/2001 | Esrock |
| 6,277,003 B1 | 8/2001 | Fernwood et al. |
| 6,283,750 B1 | 9/2001 | Esrock |
| 6,290,503 B1 | 9/2001 | Lemon et al. |
| 6,293,792 B1 | 9/2001 | Hanson |
| 6,293,856 B1 | 9/2001 | Hertz et al. |
| 6,439,966 B2 | 8/2002 | Bruns et al. |
| 6,485,303 B1 | 11/2002 | Goldman et al. |
| 2002/0016137 A1* | 2/2002 | Bruns et al. ............ 451/41 |
| 2002/0137005 A1 | 9/2002 | Cevey et al. |
| 2004/0106081 A1* | 6/2004 | Karazivan et al. ...... 433/29 |
| 2005/0032017 A1* | 2/2005 | Levy ........................ 433/29 |

FOREIGN PATENT DOCUMENTS

| | | |
|---|---|---|
| EP | 0 592 082 | 1/1999 |
| EP | 0 713 687 | 7/2001 |
| WO | WO 90/12557 | 11/1990 |
| WO | WO 98/17198 | 4/1998 |
| WO | WO 98/32406 | 7/1998 |
| WO | WO 98/57597 | 12/1998 |
| WO | WO 99/30633 | 6/1999 |
| WO | WO 00/35370 | 6/2000 |

* cited by examiner

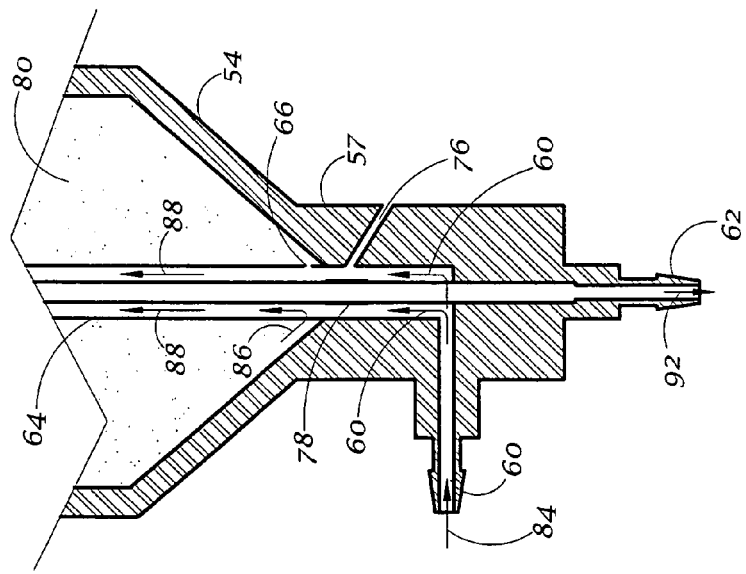
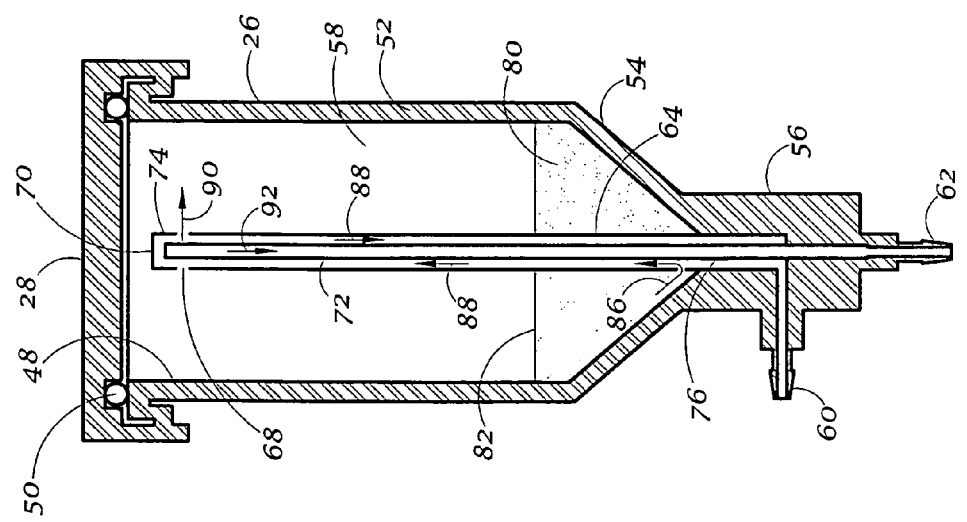
Fig. 6
Fig. 5

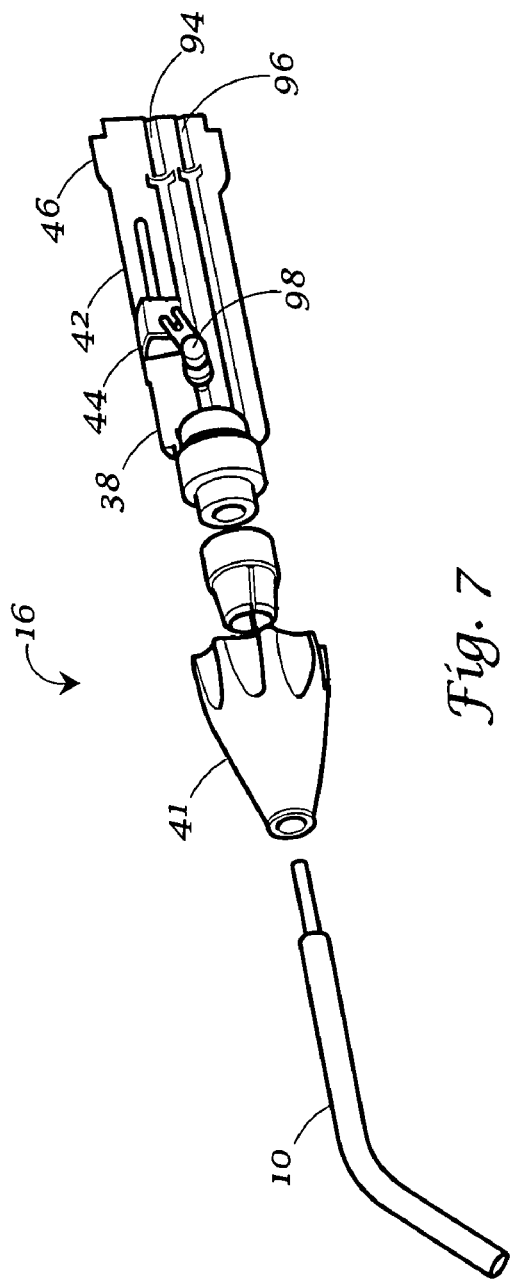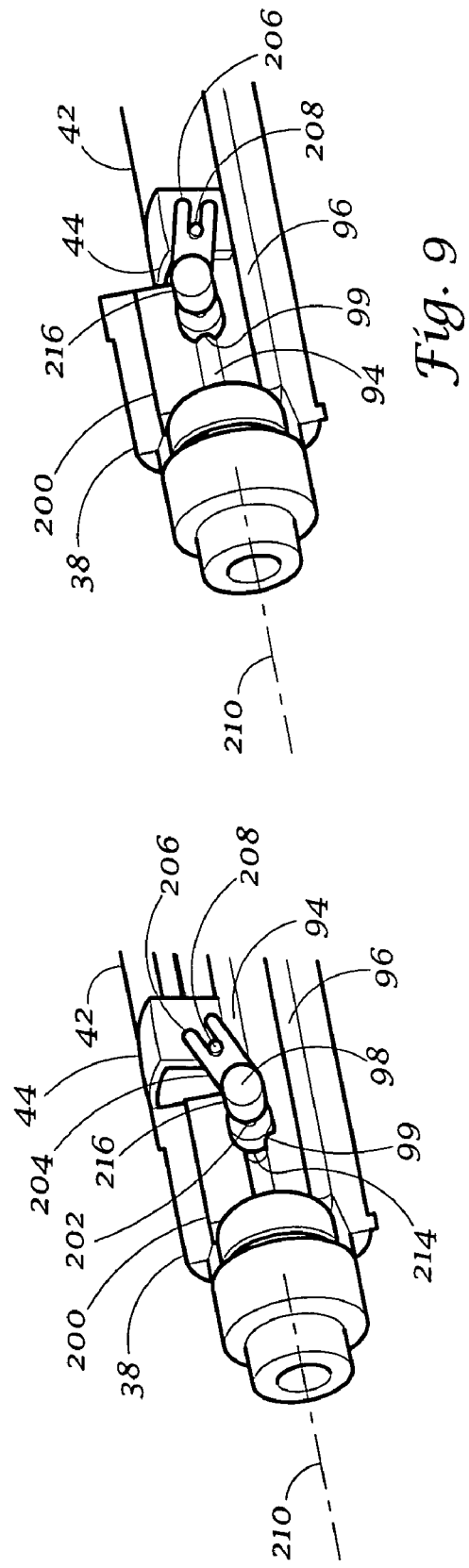

AIR POLISHING PROPHYLAXIS SYSTEM

BACKGROUND OF THE INVENTION

The present invention relates generally to a dental apparatus, and more specifically relates to an air polishing prophylaxis system for selectively applying particles entrained in a pressurized fluid flow stream to a tooth surface.

In the dental industry, an apparatus employing pressurized fluids can be used to entrain powdered abrasive particles in the pressurized fluid flow stream, the entrained pressurized gas flow stream being applied to a tooth surface to remove discolorations, soft calculus, extrinsic stains and to polish tooth surfaces. Typically, the apparatus includes a container for securing the abrasive material that is connected to the hand piece used by the dental professional. This has numerous disadvantages. When the container is directly assembled to the hand piece, the configuration adds weight and bulk to the hand piece, leading to premature grip fatigue and discomfort for the dental professional. In this configuration, the container is relatively small to minimize weight and bulk, but the duration of use before refilling of the container is required is thereby limited. By virtue of the container filled with abrasive material being constantly shifted and rotated as the hand piece is operated, the rate of application of the abrasive material is inconsistent. However, even if the container were to be maintained in a level orientation during use, the problem of inconsistent application persists. Pressurized gas introduced into the container entrains a portion of the powdered abrasive material in the container to form a "cloud" within the container, a portion of the cloud being drawn from the container for application on teeth. Typically, as abrasive material is expended, the amount of powdered abrasive material remaining within the container is reduced, which decreases the density of abrasive material in the cloud. The concentration of powdered abrasive material entrained in the cloud becomes reduced, resulting in a decreased application level of abrasive material. The inconsistent application level of powdered polishing material provides an inconsistent polishing rate to teeth, which further complicates the dental professional's task.

Another problem associated with the application of the powdered abrasive material of a dental apparatus is its tendency to clog the apparatus, especially when the abrasive material is sodium bicarbonate in a free flow agent, which is water-soluble. These materials tend to agglomerate, especially in the extremely small passages used with dental apparatus.

What is needed is a dental abrading apparatus that is lightweight and comfortable to use, having an enlarged container for holding greater amounts of powdered abrasive material, the powdered abrasive material being applied at a consistently uniform rate irrespective the amount of powdered abrasive material in the container. Additionally, a dental polishing apparatus is needed that is less susceptible to clogging by the powdered abrasive material.

SUMMARY OF THE INVENTION

The present invention is directed to a dental instrument including a body, the body including an enclosed container for holding abrasive particles, the body having a first conduit extending inside the container and in fluid communication with the interior of the container. The container includes a first removable, sealed end and a second end opposite the first end. The first conduit extends within the container generally from the second end of the container toward the first removable sealed end, the first conduit being substantially closed towards the first end of the container. The first conduit includes at least one opening substantially adjacent the second opposed end to provide fluid communication from the interior of the container into the first conduit. At least one aperture is disposed between the at least one opening and the substantially closed end of the first conduit to provide fluid communication with the interior of the container. The first conduit includes a passageway extending across the boundary of the container to its exterior to provide a flow path from the exterior of the container into the passageway. A restriction is formed in the first conduit between the at least one opening and the passageway. A second conduit extends inside the first conduit adjacent the substantially closed end of the first conduit and in fluid communication with the first conduit, the second conduit extending away from the substantially closed end of the first conduit. A source of pressurized fluid is connected to the passageway to provide fluid to the first conduit. As the pressurized fluid approaches the restriction, the pressure is further increased and velocity of the fluid is reduced. As the highly pressurized fluid passes the restriction, the pressure of the fluid drops and the velocity of the fluid increases, thereby creating a suction to draw fluid from the interior of the container. Abrasive particles are thus drawn into the first conduit through the opening and are entrained into the increased velocity fluid, creating a stream of particles entrained in the fluid. The stream moves toward the substantially closed end of the first conduit. The pressure of the fluid quickly stabilizes in the first conduit after passing the opening. A portion of the pressurized fluid exits through the aperture, along with some of the entrained particles. The remainder of the stream passes into the second conduit and moves away from the closed end of the first conduit. The pressurized fluid exits the aperture out of the conduit and into the interior of the container, providing a downward force on abrasive particles in the container, urging the particles downward and assisting the suction pressure in entraining the particles into the pressurized fluid at the opening. The second conduit includes a channel extending across the boundary of the container.

The present invention is further directed to a dental instrument including a body that includes an enclosed container having a removable portion for holding abrasive particles, the body having a conduit extending inside the container and in fluid communication with the interior of the container. The conduit includes a passageway extending across the boundary of the container to its exterior at a first location to provide a flow path from the exterior of the container into the passageway, the conduit including a channel extending across the boundary of the container to its exterior at a second location to provide a flow path from the channel to the exterior of the container. The conduit generally extends within the container from the first location of the container toward the second location of the container, the conduit including at least one opening to provide fluid communication from the interior of the container into the conduit, at least one aperture disposed between the at least one opening and the second location of the container in fluid communication with the interior of the container. A restriction is formed in the conduit between the at least one opening and the passageway, and a source of pressurized fluid is connected to the passageway to provide pressurized fluid to the conduit. Pressurized fluid flowing through the conduit into the container passes the restriction, creating a reduced pressure adjacent the at least one opening to draw abrasive particles from the interior of the container into the conduit. Abrasive particles are entrained in the pressurized fluid flowing in the conduit toward the at least one apertures, an amount of the particle-laden pressurized fluid flowing through the at least one apertures to the interior of the container. The remaining portion of the particle-laden pressurized fluid flows past the at least one apertures of the conduit and then the channel to exit the container.

The present invention still further includes a dental apparatus including a body connected to a pressurized fluid source and a pressurized liquid source. The body includes an enclosed container to hold abrasive particles, the container selectably entraining abrasive particles in the pressurized fluid. A first valve is configured to selectively control the flow of pressurized fluid from the pressurized fluid source and pressurized liquid from the pressurized liquid source to the body. A second valve is configured to selectively control the flow of pressurized fluid through the body and the flow of a pressurized liquid through the body. A tip is in fluid communication with a first line and the body for delivering the entrained pressurized fluid to the tip. A second line is in fluid communication with the tip and the body for delivering the pressurized liquid to the tip. A first conduit extends inside the container and in fluid communication with the interior of the container, the first conduit generally extending within the container from the second end of the container toward the first end, the first conduit being substantially closed toward the first end. The first conduit includes at least one opening substantially adjacent the second opposed end to provide fluid communication from the interior of the container into the first conduit, at least one aperture disposed between the at least one opening and the substantially closed first end of the first conduit in fluid communication with the interior of the container. The first conduit includes a passageway extending across the boundary of the container to its exterior to provide a flow path from the exterior of the container into the passageway. A restriction is formed in the first conduit between the at least one opening and the passageway. At least a portion of the second conduit extends inside the first conduit adjacent the substantially closed end of the first conduit and in fluid communication with the first conduit, the second conduit extending away from the substantially closed end of the first conduit. The second conduit includes a channel extending across the boundary of the container in fluid communication with the first line. The pressurized fluid source is connected to the passageway to provide pressurized fluid to the first conduit. Pressurized fluid flowing through the first conduit into the container passes the restriction, creating a reduced pressure adjacent the at least one opening to draw abrasive particles from the interior of the container into the first conduit. Abrasive particles are entrained in the pressurized fluid flowing in the first conduit toward the substantially closed end, an amount of the particle-laden pressurized fluid flowing through the at least one apertures to the interior of the container. The remaining portion of the particle-laden pressurized fluid flows past the substantially closed end of the first conduit and into the second conduit and then the channel to exit the container.

The present invention still yet further includes a dental instrument including a body having a securing device for securing the body to a dental unit, the body including an enclosed container having a removable portion for holding abrasive particles. The body has a conduit extending inside the container and in fluid communication with the interior of the container, the conduit including a passageway extending across the boundary of the container to its exterior at a first location to provide a flow path from the exterior of the container into the passageway. The conduit includes a channel extending across the boundary of the container to its exterior at a second location to provide a flow path from the channel to the exterior of the container, the conduit generally extending within the container from the first location of the container toward the second location of the container. The conduit includes at least one opening to provide fluid communication from the interior of the container into the conduit, at least one aperture disposed between the at least one opening and the second location of the container in fluid communication with the interior of the container. A restriction is formed in the conduit between the at least one opening and the passageway, and a source of pressurized fluid is connected to the passageway to provide pressurized fluid to the conduit. Pressurized fluid flows through the conduit into the container passing the restriction, creating a reduced pressure adjacent the at least one opening to draw abrasive particles from the interior of the container into the conduit. Abrasive particles are entrained in the pressurized fluid flowing in the conduit toward the at least one apertures, an amount of the particle-laden pressurized fluid flowing through the at least one apertures to the interior of the container. The remaining portion of the particle-laden pressurized fluid flow past the at least one apertures of the conduit and then the channel to exit the container.

The present invention further includes a method for cleaning a dental instrument. The steps include: providing a dental instrument that selectively provides at least one of a pressurized first fluid and a pressurized second fluid to a patient through at least one passage in the dental instrument while the dental instrument operates in a first mode, the dental instrument being configured for connection to at least one pressurized fluid source, the at least one pressurized fluid source providing at least one pressurized fluid to the dental instrument, enabling the dental instrument to provide the at least one of the pressurized first fluid and the pressurized second fluid; and operating the dental instrument in a purge mode, the purge mode directing the at least one pressurized fluid from the at least one pressurized fluid source to flow through a predetermined portion of the at least one passage to purge the remaining first fluid and the second fluid from the at least one passage.

The terms abrasive particles, abrasive material, or abrasive powder refer to the material used to fill the container for use with the apparatus of the present invention, and may be used interchangeably.

One advantage of the present invention is that it has a hand piece of reduced weight and bulk.

Another advantage of the present invention is that it does not require refilling with abrasive material as often.

A further advantage of the present invention is that it provides a consistent delivery rate of abrasive material.

A yet further advantage of the present invention is that it has a purge cycle to reduce the chance of clogging by abrasive material and to remove water in the passageways of the apparatus.

An additional advantage of the present invention is that it is compatible with standard dental units.

A further advantage of the dental apparatus of the present invention is that it can be conveniently attached to a standard dental unit to prevent damage to both the dental apparatus and the dental unit.

A still further advantage of the present invention is that it is compact in construction.

A yet further advantage of the present invention is that the hand piece and tip or nozzle are autoclavable.

Other features and advantages of the present invention will be apparent from the following more detailed description of the preferred embodiment, taken in conjunction with the accompanying drawings which illustrate, by way of example, the principles of the invention.

BRIEF DESCRIPTION OF THE DRAWINGS

FIG. 5 is a cross section of an embodiment of a container securing abrasive material of the present invention.

FIG. 6 is an enlarged, partial cross section of the embodiment of the container of the present invention.

FIG. 7 is an exploded perspective view of an embodiment of a hand piece and tip of the present invention.

FIG. 8 is an enlarged, partial cross section of the embodiment of the hand piece of FIG. 7 in a closed position of the present invention.

FIG. 9 is an enlarged, partial cross section of the embodiment of the hand piece of FIG. 7 in an open position of the present invention.

Wherever possible, the same reference numbers will be used throughout the drawings to refer to the same or like parts.

DETAILED DESCRIPTION OF THE INVENTION

Figure 1:
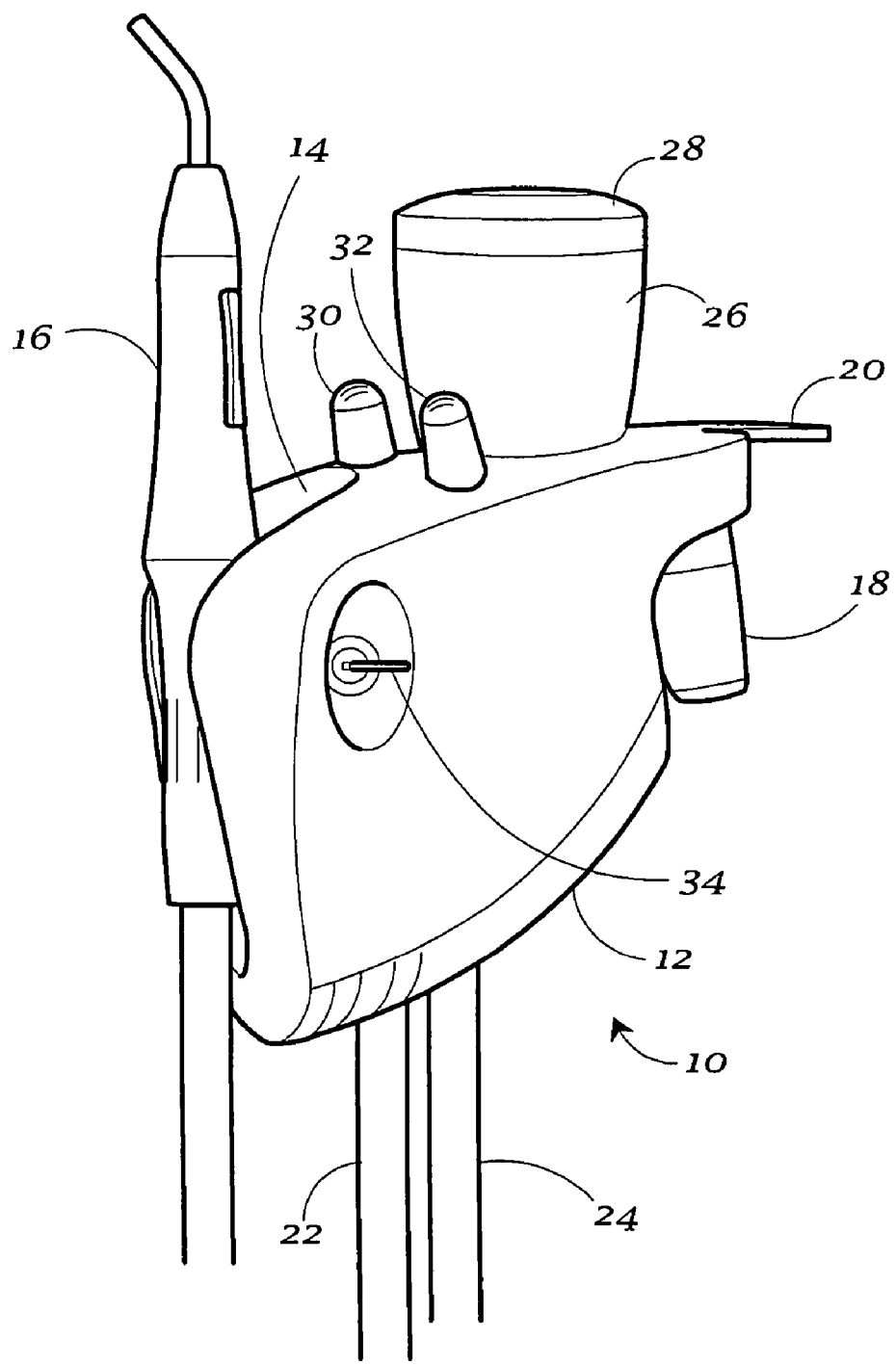
FIG. 1 is a perspective view of an embodiment of a dental abrading apparatus of the present invention.

One embodiment of the dental apparatus 10 of the present invention is depicted in FIG. 1. Dental apparatus 10 includes a control unit 12 having a cradle 14 for securing a hand piece 16 when hand piece 16 is not in use. A securing device, such as a post 18, extends from control unit 12 to secure control unit 12 to a retainer found in standard dental units. A locking mechanism 20, such as a movable latch, maintains control unit 12 in its secured position from being inadvertently moved and damaged. A cable 22 from a standard dental unit, attaches to a connector on control unit 12, which supplies pressurized water and air to control unit 12. Providing the pressurized air and water to hand piece 16 from control unit 12 is a cable 24. Abrasive particles, such as sodium bicarbonate or aluminum trihydroxide (ATH) that have been rendered to a powder, are the source of dental abrasion of apparatus 10. These abrasive particles are added to a container 26 on the control unit 12 by removing and then replacing a lid 28 on the container 26. In operation, as discussed in further detail below, upon activation of valves within the control unit 12 and the hand piece 16, pressurized air entering control unit 12 through cable 22 entrains a consistent concentration of abrasive particles which pass through cable 24 and hand piece 16 for application to teeth.

Figure 2:
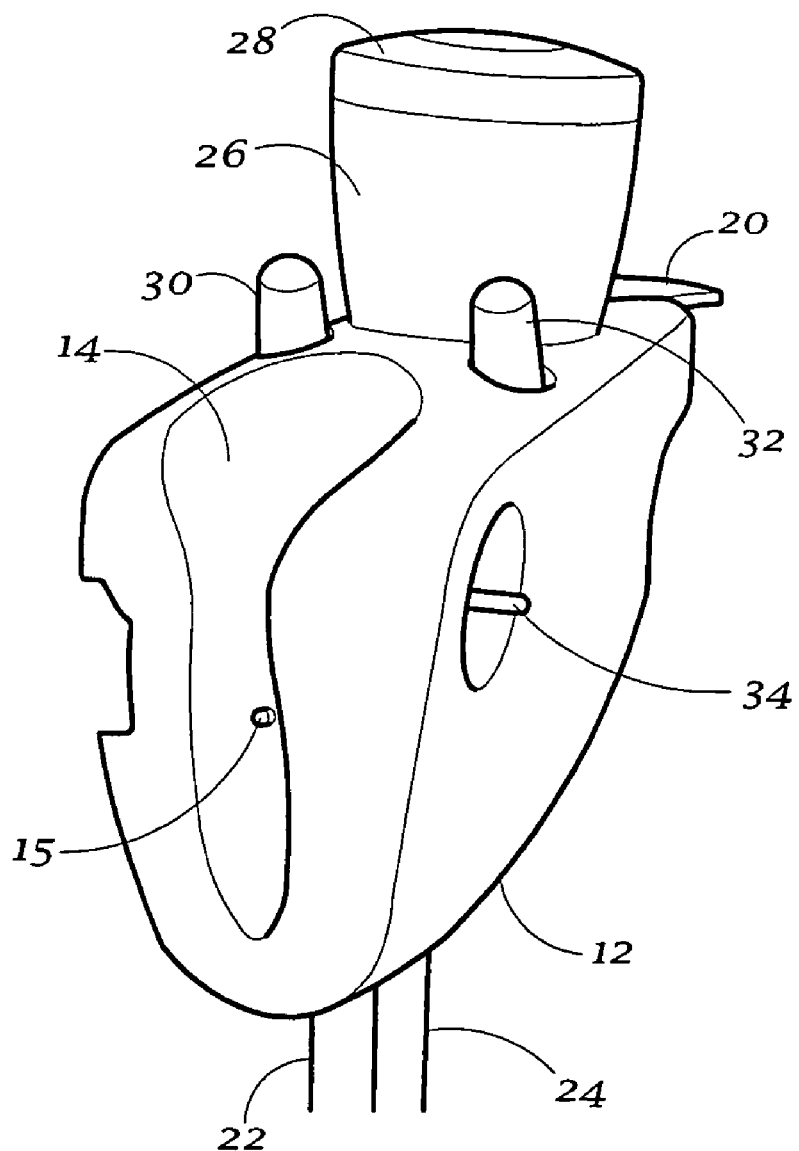
FIG. 2 is a perspective view of the embodiment of a dental abrading apparatus of the present invention.
Figure 4:
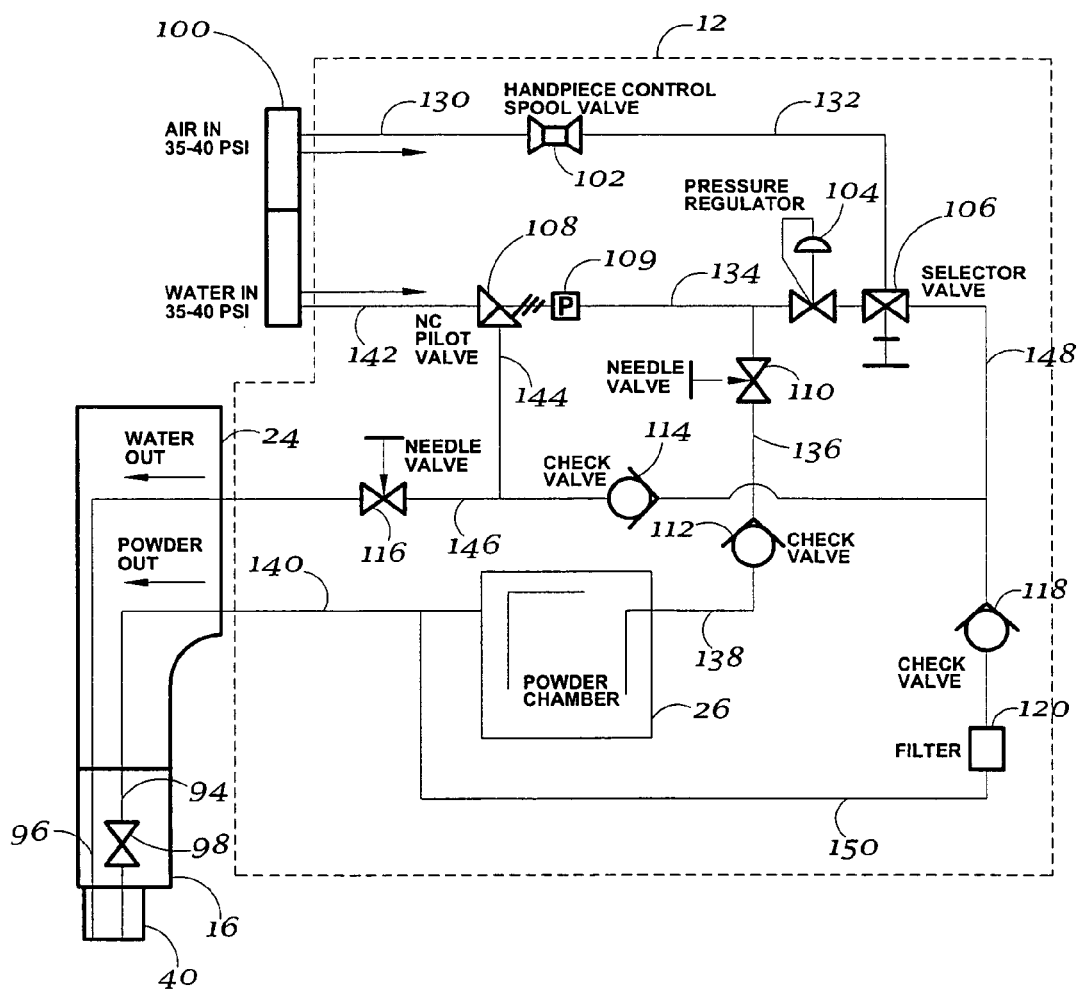
FIG. 4 illustrates a schematic detailing flow control of an embodiment of a control unit of the present invention.

Referring to FIGS. 1, 2 and 4 control unit 12 has an attractive, compact construction that is compatible with standard dental units. Post 18 preferably has a sloped profile for ease of insertion in an aperture or tool holder of a standard dental unit (not shown). After insertion, locking mechanism 20 provides an interference between locking mechanism 20 and the dental unit to prevent inadvertent removal from the tool holder, while allowing for some freedom of movement of the control unit 12 in its secured position. Cradle 14 includes a valve button 15 that controls a valve 102, such as a spool valve, disposed inside the control unit 12. Valve button 15 is actuated when the hand piece 16 is placed in the cradle 14. When the hand piece 16 is placed in the cradle 14 which actuates the valve button 15, the dental apparatus 10 is no longer in use, and the actuated valve button 15 closes the valve 102 to prevent the flow of pressurized air to path 132 of the control unit 12. A selector switch 34 in control unit 12, such as a toggle switch, controls a selector valve 106 which places the control unit 12 in a run mode when the selector switch 34 is actuated to a first position, or a purge mode when the selector switch 34 is actuated to a second position. The purge mode is provided to prevent clogging of the control unit 12, cable 24 and hand piece 16, by removing abrasive particles disposed in paths with pressurized air. However, the purge mode is also provided to remove water from paths in the control unit 12, cable 24 and hand piece 16 with pressurized air. The flow of pressurized air through control unit 12 is selectively controlled by actuating a knob 32 that selectively opens or closes a valve 110, such as a needle valve, in control unit 12. Similarly, the flow of pressurized water through control unit 12 in the run mode is selectively controlled by actuating a knob 30 that selectively opens or closes a valve 116, such as a needle valve, in control unit 12. A pressure regulator 104 for regulating the incoming pressurized air received from the dental unit is preferably set during assembly of the dental apparatus 10 and not adjusted by an operator in normal use.

Figure 3:
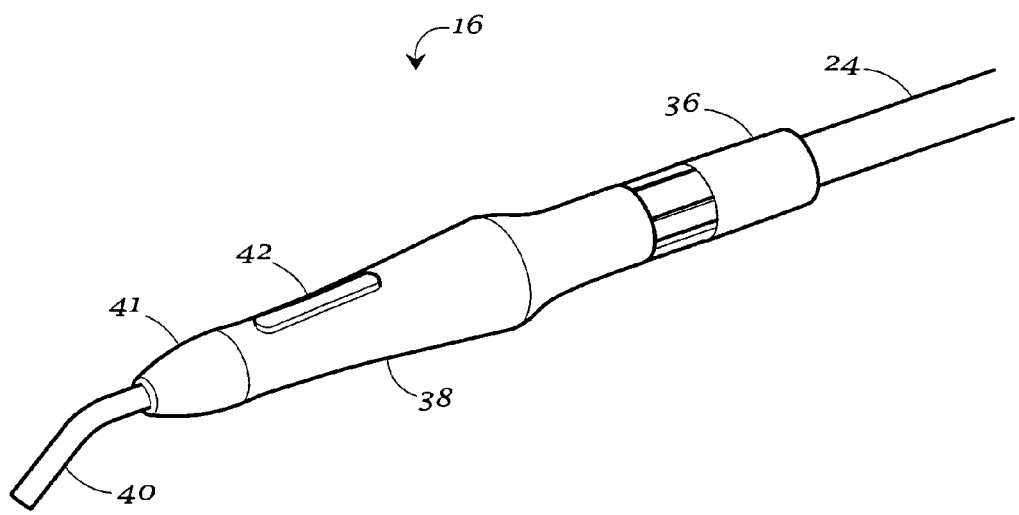
FIG. 3 is a perspective view of an embodiment of a hand piece and tip of the present invention.

Referring to FIG. 3, in a preferred embodiment hand piece 16 includes a grip 38 that extends from a thumb nut 41 at one end of the hand piece 16. The grip 38 extends to a swivel 36 at the other end of the hand piece 16 for connecting to cable 24. The invention is not so limited, and the grip 38 and the thumb nut 41 can be configured to be a single removable element, as the invention is not dependent upon the arrangement of the thumb nut 41 and the grip 38, as any workable arrangement is acceptable. Preferably, the hand piece 16 can be detached from the cable 24 and the tip 40 can be removed from the hand piece 16 and directly placed in an autoclave, which typically subjects the hand piece 16 and the tip 40 to elevated temperatures of about 273° F. (134° C.) for a sufficient amount of time to kill harmful bacteria that could otherwise be spread from one patient to another. It is also preferable that the hand piece 16 and the tip each be survivable to at least about 1,000 cycles. While it is possible to construct most of the hand piece components of metal, metal has a high density and would result in an extremely heavy hand piece. Optionally, tip 40, also referred to as a nozzle, of hand piece 16 is disposable, and thus could be constructed of non-autoclable materials, if desired. In a preferred embodiment, internal grip components may be constructed of polypropylene or other medically approved materials, such as RADEL® which is a registered trademark of Union Carbide Corporation, also referred to as polyarylethersulfone. However, it is preferred that at least the outer portion of the grip 38 is composed of a soft, resilient material that provides high friction and tactile feel and comfort. Preferably, a layer of a thermoplastic elastomer, such as SANTOPRENE®, a registered trademark of Monsanto Company, or silicon or other high temperature elastomer is bonded to the inner substrate of the grip. It is preferable that this bond will not delaminate during autoclaving or after many autoclave cycles, the bond formed by an adhesive, heat, chemical bond or by any other bonding technique that secures the outer layer to the inner substrate of the grip 38.

Referring to FIGS. 7-9, grip 38 of hand piece 16 includes a passageway 94 for directing the flow of a first fluid, such as mixture of a gas and powder, to tip 40. Similarly, a passageway 96 for directing the flow of a second fluid, such as pressurized water or any other liquid provided by the dental unit, to the end of tip 40. While the dental apparatus 10 is in operation, water for rinsing the region of interest in the mouth flows substantially unabated through passageway 96 of hand piece 16, and is directed from the end of tip 40. However, it is desirable to selectively control the flow of the regulated mixture 92 (FIG. 6) of entrained abrasive particles in the pressurized gas that flows through passageway 94 of hand piece 16 while the dental apparatus 10 is in operation. A valve 98, such a barrel valve, is used to effect this selective flow control of the regulated mixture 92 (FIG. 6) of entrained abrasive particles in the pressurized gas. Valve 98 includes a body portion 214 having a through aperture 99 formed therein. Body portion 214 extends to a cylindrical portion 216. Preferably, body portion 214 and cylindrical portion 216 are substantially axially aligned to rotate about an axis of rotation 210. Extending radially outward from cylindrical portion 216 is an arm 204 that further extends to a pair of fingers 206 opposite the cylindrical portion 216. A valve button 42 preferably is cantilevered to rotate an end 44 of valve button 42 substantially transverse to the length of the grip 38 about an axis 46. A post 208 adjacent to end 44 of valve button 42 slidably engages fingers 206.

As the end 44 of valve button 42 is actuated about axis 46, post 208 traces an arc about axis 46 as post 208 slides between fingers 206. By virtue of the sliding contact between fingers 206 and post 208, arm 204 is urged into rotational movement about axis 210 which likewise urges cylindrical portion 216 and body portion 214 into rotational movement about axis 210. Sufficiently rotating body portion 214 about axis 210 rotates aperture 99 into or out of fluid communication with passageway 94. When valve button 42 is in a non-actuated position, outward in the embodiment shown in FIG. 8, aperture 99 is not in fluid communication with passageway 94. However, when valve button 42 is in a fully actuated position, inward in the embodiment shown in FIG. 9, aperture 99 is in full fluid communication with passageway 94. One having skill in the art appreciates that the valve button 42 can be actuated to any position between the non-actuated position and the fully actuated position as desired so that aperture 99 can be selectively positioned to provide a full range of flow control of the regulated mixture 92 (FIG. 6) of entrained abrasive particles in the pressurized gas stream through passageway 94. One skilled in the art will recognize that the function of the valve button 42 is to control flow in the aperture 99, and the physical position of the button is immaterial as long as the function is achieved. In an alternative embodiment, the valve button 42 can be configured to be either fully open or fully closed.

Valve 98 is received in grip 38 by a closely toleranced recess 200 that provides a fluid tight seal between body portion 214 and recess 200 when valve 98 is rotated about axis 210 so that aperture 99 is not in fluid communication with passageway 94. To further help provide a fluid tight seal between valve 98 and grip 38, an O-ring 202 can be disposed between body portion 214 and cylindrical portion 216. Thus, the closely toleranced fit between recess 200 and body portion 214 to be fluid tight. However, if as a result of wear between recess 200 and body portion 214, it is believed the seal will be maintained due to the deposition of abrasive particles between recess 200 and body portion 214. Therefore, when valve button 42 is oriented in the non-actuating position, the regulated mixture 92 of entrained abrasive particles in the pressurized gas stream will not flow along passageway 94 and around valve 98 to tip 40 of the hand piece 38.

Referring to FIGS. 1 and 4, the control unit 12 operates to selectively provide pressurized water and abrasive particle-entrained air to the hand piece 16. Both pressurized water and air are provided to control unit 12 by virtue of a connection to a standardized interface with a dental unit (not shown), such as an ISO 9168, also referred to as Midwest 4-hole connection. Although the standardized interface can also provide a vacuum line for exhaust air, only the pressurized air and water connections are used by the control unit 12. To prevent the pressurized air and water from accessing the control unit 12, a valve 100 is located in the dental unit that is preferably operated by a foot switch, both of which are part of the dental unit. Thus, the valve 100 remains in a closed position, blocking the flow of pressurized air and water into the control unit 12 until the foot switch is depressed.

Once the foot switch is depressed and valve 100 is opened, pressurized air flows along path 130 to valve 102 that corresponds to the presence of the hand piece 16 in the cradle of the control unit 12. In other words, valve 102 is normally in a closed position when the valve button 15 in cradle 14 is activated, i.e., when the hand piece 16 is installed in the cradle 14. Removing the hand piece 16 from the cradle 14 places the valve button 15 in a non-activated position, which opens valve 102, permitting pressurized air to flow past valve 102 along path 130 to path 132 to encounter a selector valve 106. The term "path" can refer to a passageway formed in the control unit 12 body, but can also refer to lines used to connect components in the control unit, as desired. The term "path" or "line" may be used interchangeably. Selector valve 106, which is controlled by selector switch 34, directs pressurized air along path 148 if the selector switch 34 is actuated to a position that corresponds to the purge mode. However, if the selector switch 34 is actuated to a position that corresponds to the run mode, or standard operating mode, pressurized air is directed along path 134 through a pressure regulator 104 to a valve 108, such as a pilot valve. Valve 108 is normally closed, and blocks the flow of pressurized water that flows along path 142 when valve 100 is opened to permit the flow of pressurized water from the dental unit to the control unit 12. However, when valves 100, 102 are opened so that pressurized air flows along path 130, 132 and 134, pressurized air fills an air cylinder disposed within the valve 108 which opens valve 108, permitting the flow of pressurized water past valve 108 along path 144 to path 146 to a needle valve 116 that is controlled by knob 30. The pressurized water flows along path 146 away from the control unit 12 through cable 24 for delivery to the hand piece 16. Back flow of the pressurized water along path 146 is prevented by check valve 114.

Pressurized air flowing along path 134 that is not directed into the air cylinder of valve 108 flows along path 136 through a valve 110, such as a needle valve, which is controlled by knob 32. Once the pressurized air flows past valve 110 along path 136, the pressurized air encounters and flows through a check valve 112 and continues along path 138 to the powder container 26. Upon reaching the powder container 26, abrasive particles, typically in the form of powder, which are inside the powder container 26 becomes entrained in the flow of the pressurized air, that is described in further detail below. Abrasive powder entrained in the pressurized air is discharged from the powder chamber 26 along path 140 to cable 24, the abrasive powder entrained pressurized air, being prevented from flowing past check valve 118 along path 150.

The operation of the purge mode of the control unit 12 is now discussed. Once the foot switch from the dental unit is depressed and valve 100 is opened, pressurized air flows along path 130 to valve 102 that corresponds to the presence of the hand piece 16 in the cradle of the control unit 12. In other words, valve 102 is normally in a closed position when the valve button 15 in cradle 14 is activated, i.e., when the hand piece 16 is installed in the cradle 14. Removing the hand piece 16 from the cradle 14 places the valve button 15 in a non-activated position, which opens valve 102, permitting pressurized air to flow past valve 102 along path 130 to path 132 to encounter a selector valve 106. Selector valve 106, which is controlled by selector switch 34, directs pressurized air along path 148 if the selector switch 34 is actuated to a position that corresponds to the purge mode. When selector valve 106 is in purge mode, path 134 is open to the atmosphere, allowing valve 108 to close. The pressurized air flowing along 148 then flows along path 146 and encounters and flows through check valve 114, then through needle valve 116 before reaching cable 24. Referring back to FIG. 7, one skilled in the art appreciates that pressurized air flowing along cable 24 to hand piece 16 is directed along passageway 96 of the grip 38 and directed through the tip 40 to remove water that is contained in or in communication with the paths 146, the cable 24 and passageway 96 in the hand piece 16.

Similarly, the portion of the pressurized air flowing along path 148 that does not branch off to flow along path 146 encounters and flows through a check valve 118 and a filter 120 and then flows along path 150 before flowing along path 140. The pressurized air flowing along path 140 exits control unit 12 and flows through cable 24 before reaching passageway 94 of the hand piece 16. When the valve button 42 in the grip 38 of the hand piece 16 is actuated to an actuated position (i.e., depressing end 44 of the valve button 42), pressurized air is directed through the passageway 94 and through the tip 40 to remove residual abrasive powder that is contained in or in communication with the paths 148, 150, 140, cable 24 and passageway 94 in the hand piece 16 to prevent clogging of the dental apparatus 10.

For pressurized water to flow from the dental unit through the tip 40 of hand piece 16, both valve 100, as controlled by the foot switch, and valve 102, as controlled by the hand piece presence valve button 15, must be in an open position. Once valve 100 and valve 102 are open, pressurized water flows through the control unit 12, cable 24 and hand piece 16 without restriction, typically for rinsing purposes. For pressurized air to flow from the dental unit through the tip 40 of hand piece 16, the pressurized air having abrasive material entrained in powder container 26 of control unit 12 as described in further detail below, valve 100, as controlled by the foot switch, valve 102, as controlled by the hand piece presence valve button 15, and valve 98, as controlled by valve button 42, must each be in an open position. That is, if valves 100, 102 are open, pressurized water flows from the dental unit to the tip 40 of the hand piece 16, but flow of abrasive powder-entrained pressurized air does not flow through valve 98 when valve 98 is in a closed position.

Referring to FIGS. 4-6, the operation of abrasive powder container 26 is now discussed. Container 26 preferably includes a cylindrical portion 52 having an open first end 48, which cylindrical portion 52 extending to a sloped portion 54. Sloped portion 54 connects to a base 56 disposed at a second end 57 that is opposite the first end 48, the base 56 preferably providing both a passageway 60 into container 26 and a channel 62 from container 26. To provide container 26 with a substantially fluid tight seal, lid 28 which fits over first end 48 can include an O-ring 50, O-ring 50 sealingly contacting opposed surfaces of lid 28 and first end 48 of container 26 when lid 28 is sufficiently engaged with container 26 so that O-ring 50 is compressed between lid 28 and first end 48. Collectively, cylindrical portion 52, sloped portion 54, base 56 and lid 28 define an enclosed interior 58 capable of receiving pressurized air 84 from passageway 60 within control unit 12 along path 138 to entrain a portion of the abrasive powder 80 in the pressurized air 84 for delivering the regulated mixture 92 of abrasive powder-entrained pressurized air through channel 62. The regulated mixture 92 of abrasive powder-entrained pressurized air flows through channel 62 along path 140 in control unit 12, through cable 24, and through hand piece 16 for application to teeth. It is to be understood that cylindrical portion 52 could define any closed geometry, and that a sloped portion 54 is not required, but is present in a preferred embodiment to help direct abrasive powder 80 to the interface between sloped portion 54 and base 56. Additionally, a preferred construction of cylindrical portion 52, sloped portion 54 and base 56 are of unitary construction.

Base 56 preferably includes the passageway 60 for receiving pressurized air 84 into the interior 58, and channel 62 for discharging the regulated mixture 92 of abrasive powder-entrained pressurized air from interior 58. Extending from the juncture of base 56 and sloped portion 54 is a first conduit 64, such as a tube. In a preferred embodiment, at least one opening 66, and as shown in FIG. 6 as a pair of apertures 66, such as a single through hole, is formed in first conduit 64. Preferably, apertures 66 are disposed adjacent the juncture between sloped portion 54 and base 56, since this permits substantially all of the abrasive powder 80 to flow from the interior 58 through apertures 66. First conduit 64 extends upwardly inside interior 58 to a cap 70. Adjacent cap 70, at least one aperture 68, and as shown in FIG. 5, preferably at least two apertures 68 are formed in first conduit 64. The size, number and location of the apertures 68 with respect to end 70 can be controlled in view of factors that include, but are not limited to, the size of the particles of abrasive powder, density of the abrasive powder and the magnitude of the pressurized air that is applied by the dental unit to provide a desired regulated concentration of entrained abrasive material mixture 92.

A second conduit 72 is preferably disposed inside of first conduit 64 to deliver the regulated mixture 92 of entrained abrasive powder in the pressurized gas, although it is only necessary for an end 74 of second conduit 72 to actually be disposed inside first conduit 64. Preferably, end 74 of second conduit 72 is adjacent the first end 48 of container 26. That is, in an alternate embodiment, second conduit 72 can extend outside of first conduit 64 and through container 26 at any point to discharge the regulated mixture 92 of entrained abrasive powder in the pressurized gas from interior 58. However, returning to a preferred embodiment as shown, second conduit 72 extends substantially concentrically inside of first conduit 64 from end 74 toward base 56. Adjacent apertures 66, a restriction 76 in flow area between the inside surface of first conduit 64 and the outside surface of second conduit 72 is formed, such as a radially outwardly extending protrusion. Alternately, restriction 76 can be defined by a reduction in the area of flow contained within the inside surface of first conduit 64, or a combination of increased area of flow contained within the outer surface of second conduit 72 and a decreased area of flow contained within the inner surface of first conduit 64. It is also possible that size of restriction 76 can be varied, if desired by any number of techniques known in the art, such as inserting a controllably expandable material between the first and second conduits 64, 72. The location of the restriction 76 with respect to apertures 66 is preferably such that when pressurized air 84 is directed to flow through passageway 60 and into interior 58 by flowing between first conduit 64 and second conduit 72, upon the pressurized air 84 encountering restriction 76, the velocity of the pressurized air increases and the pressure is reduced adjacent the restriction 76 in accordance with the Venturi effect. Due to the reduced pressure inside first conduit 64 adjacent apertures 66 with respect to the pressure outside first conduit 64 adjacent 66 in interior 58, abrasive powder 86 is drawn through opening 66 and entrained in the pressurized air to become a mixture 88 of entering abrasive powder 86 and pressurized air 84 flowing inside first conduit 64 between first conduit 64 and second conduit 72.

As mixture 88 flows upwardly toward the first end 48 between first conduit 64 and second conduit 72 the pressure inside first conduit 64 increases from the pressure level adjacent openings 66 to a level substantially similar to that achieved prior to the mixture 88 encountering the restriction 76. Additionally, the venturi effect may help to achieve a higher concentration of entrained abrasive powder within the flow of pressurized air than would otherwise be possible. The mixture 88 then is directed toward aperture 68, and as shown, a pair of apertures 68. Since abrasive powder 68 is drawn through opening 66 adjacent the second end 57 of the container 26, the pressure level in the interior 58 is initially reduced, and is less than the pressure of mixture 88. A pressure equilibrium is achieved relatively quickly inside the container 26. An amount of the mixture 88, a mixture 90, is drawn through the apertures 68 into the interior 58 of the container 26. The remaining portion of the mixture 88 is then directed toward cap 70 before entering end 74 of second conduit 72. An amount of the entrained abrasive powder of mixture 88 strikes cap 70 of first conduit 64 and passes through apertures 68 for return to interior 58. Apertures 68 are necessary in first conduit 64, otherwise, a vacuum will form in the interior 58 of container 26, which shuts off the flow of particles through openings 66 into the first conduit 64. The concentration of remaining entering abrasive powder 86 that flows in the pressurized gas, defines regulated mixture 92 which remains substantially constant irrespective the amount of abrasive powder 80 remaining in container 26, as indicated by level 82, except, of course, when level 82 is above aperature 68 or when the level 82 is adjacent apertures 66, i.e., the powder is substantially expended. Further, even when level 82 of abrasive powder 80 is above aperture 68, in the preferred embodiment, after an initial stream of abrasive powder 80 is generated, the regulated mixture 92 quickly becomes substantially constant. The regulated mixture 92 is directed through the channel 62, to exit the container 26, and ultimately through the tip 40 of the hand piece 16 as previously discussed. It has been found that when the abrasive powder size is too small, clumping of the particles occurs. When the abrasive powder size is too large, the particles will not flow properly through the apertures. The particle size will depend upon the specific operation intended by the hand piece 16 for polishing dental surfaces. It is preferred to use a distribution of particle sizes. The preferred particles for polishing are Prophy-Jet® powder, which is a sodium bicarbonate based material, and Jet-Fresh®, that is an aluminum trihydroxide (ATH) based material, both manufactured by trademark owner DENTSPLY International, Inc. However, particle size could vary significantly from the sizes used in these powders, depending upon the size of conduits 64, 72, apertures 66, 90, restriction 76, the location of the end 74 of second conduit 72 from cap 70, individually or in combination, in addition to the magnitude of pressurized air 60, as well as other operating parameters.

As stated previously, it is possible that only a portion of second conduit 72 is disposed inside of first conduit 64 and that second conduit 72 can extend through container 26 at any position in container along container 26, so long as the first and second conduits 64, 72 are correspondingly sized to accommodate the desired arrangement, and restriction 76 is formed along the inside surface of first conduit 64, i.e., if second conduit 72 does not extend past apertures 66. Similarly, first conduit 64 is not constrained to extend in a straight line from the juncture between sloped portion 54 and base 56, but to preferably extend upwardly so that apertures 90 are disposed above a desired abrasive powder level 82.

In an alternative embodiment, a single conduit can be used in place of first and second conduits 64, 72, so long as the openings 66 and apertures 68 are formed in the single conduit. The single conduit is not limited to a vertically disposed linear geometry, and can be formed in any number of curved configurations, so long as the openings 66 and apertures 68 function as previously described.

While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out this invention, but that the invention will include all embodiments falling within the scope of the appended claims.

What is claimed is:

1. A dental instrument comprising:
   a body, the body directly attached to an enclosed container, the enclosed container having a removable portion for holding abrasive particles, the body having a conduit extending inside the container and in fluid communication with the interior of the container, the conduit including a passageway extending across the boundary of the container to its exterior at a first location to provide a flow path from the exterior of the container into the passageway, the conduit including a channel extending across the boundary of the container to its exterior at a second location to provide a flow path from the channel to the exterior of the container, the conduit generally extending within the container from the first location of the container toward the second location of the container, the conduit including at least one opening to provide fluid communication from the interior of the container into the conduit, at least one aperture disposed between the at least one opening and the second location of the container in fluid communication with the interior of the container;
   a restriction formed in the conduit between the at least one opening and the passageway;
   a source of pressurized fluid being connected to the passageway to provide pressurized fluid to the conduit;
   wherein pressurized fluid flowing through the conduit into the container passing the restriction, creating a reduced pressure adjacent the at least one opening to draw abrasive particles from the interior of the container into the conduit, abrasive particles being entrained in the pressurized fluid flowing in the conduit toward the at least one apertures, an amount of the particle-laden pressurized fluid flowing through the at least one apertures to the interior of the container, the remaining portion of the particle-laden pressurized fluid flowing past the at least one apertures of the conduit and then the channel to exit the container, and
   wherein the body includes a switch capable of activating the dental instrument in one position and purging the dental instrument in a second position.

2. The dental instrument of claim 1 wherein size of the restriction is variable.

3. The dental instrument of claim 1 wherein a concentration of abrasive particles in the particle-laden pressurized fluid remains substantially constant.

4. The dental instrument of claim 1 wherein the abrasive particles are composed of sodium bicarbonate.

5. The dental instrument of claim 1 wherein the abrasive particles are composed of aluminum trihydroxide.

6. The dental instrument of claim 1 wherein the body is secured to a dental unit.

7. The dental instrument of claim 6 wherein the body includes a post.

8. The dental instrument of claim 7 wherein the body includes a securing device.

9. The dental instrument of claim 1 comprising:
a tip;
a line in fluid communication with the tip and the body for delivering the particle-laden pressurized fluid to the tip;
a valve configured to selectively control the flow of particle-laden pressurized fluid to the tip; and
wherein upon the valve being actuated to an open position, particle-laden pressurized fluid flows to the tip, and upon the valve being actuated to a closed position, the valve providing a fluid tight seal to prevent the flow of particle-laden pressurized fluid to the tip.

10. The dental instrument of claim 9 wherein the valve is configured to be either fully open or fully closed.

11. The dental instrument of claim 9 wherein the valve is configured to provide a full range of flow control.

12. The dental instrument of claim 9 comprising a hand piece interposed between the tip and the body.

13. The dental instrument of claim 12 wherein the hand piece and the tip are autoclavable.

14. The dental instrument of claim 12 wherein the hand piece and the tip are each configured to survive at least about 1,000 autoclave cycles.

15. The dental instrument of claim 12 wherein the hand piece includes a grip.

16. The dental instrument of claim 15 wherein an external portion of the grip is composed of a soft, resilient material providing high friction, tactile feel and comfort.

17. The dental instrument of claim 16 wherein the external portion of the grip is composed of a thermoplastic elastomer.

18. The dental instrument of claim 15 wherein an internal portion of the grip is composed of polypropylene.

19. The dental instrument of claim 15 wherein an internal portion of the grip is composed of polyarylethersulfone.

20. The dental instrument of claim 17 wherein the external portion of the grip is bonded to an inner substrate, the bond being capable of withstanding autoclave cycles.

21. The dental instrument of claim 15 wherein the grip includes a thumb nut to secure the tip.

22. The dental instrument of claim 21 wherein the thumb nut and the grip are configured to be a single removable element.

23. A dental instrument comprising:
a body, the body directly attached to an enclosed container, the enclosed container having a first removable end and an opposed second end for holding abrasive particles, the body having a first conduit extending inside the container and in fluid communication with the interior of the container, the first conduit generally extending within the container from the second end of the container toward the first end, the first conduit being substantially closed toward the first end, the first conduit including at least one opening substantially adjacent the second opposed end to provide fluid communication from the interior of the container into the first conduit, at least one aperture disposed between the at least one opening and the substantially closed first end of the first conduit in fluid communication with the interior of the container, the first conduit including a passageway extending across the boundary of the container to its exterior to provide a flow path from the exterior of the container into the passageway;
a restriction formed in the first conduit between the at least one opening and the passageway;
a second conduit, at least a portion of the second conduit extending inside the first conduit adjacent the substantially closed end of the first conduit and in fluid communication with the first conduit, the second conduit extending away from the substantially closed end of the first conduit, the second conduit including a channel extending across the boundary of the container;
a source of pressurized fluid being connected to the passageway to provide pressurized fluid to the first conduit;
wherein pressurized fluid flowing through the first conduit into the container passing the restriction, creating a reduced pressure adjacent the at least one opening to draw abrasive particles from the interior of the container into the first conduit, abrasive particles being entrained in the pressurized fluid flowing in the first conduit toward the substantially closed end, an amount of the particle-laden pressurized fluid flowing through the at least one apertures to the interior of the container, the remaining portion of the particle-laden pressurized fluid flowing past the substantially closed end of the first conduit and into the second conduit and then the channel to exit the container, and
wherein the body includes a switch capable of activating the dental instrument in one position and purging the dental instrument in a second position.

24. A dental apparatus comprising:
a body connected to a pressurized fluid source and a pressurized liquid source, the body directly attached to an enclosed container to hold abrasive particles, the container selectably entraining abrasive particles in the pressurized fluid;
a first valve configured to selectively control the flow of pressurized fluid from the pressurized fluid source and pressurized liquid from the pressurized liquid source to the body;
a second valve configured to selectively control the flow of pressurized fluid through the body and the flow of a pressurized liquid through the body;
a tip;
a first line in fluid communication with the tip and the body for delivering the entrained pressurized fluid to the tip;
a second line in fluid communication with the tip and the body for delivering the pressurized liquid to the tip;
a first conduit extending inside the container and in fluid communication with the interior of the container, the first conduit generally extending within the container from the second end of the container toward the first end, the first conduit being substantially closed toward the first end, the first conduit including at least one opening substantially adjacent the second opposed end to provide fluid communication from the interior of the container into the first conduit, at least one aperture disposed between the at least one opening and the substantially closed first end of the first conduit in fluid communication with the interior of the container, the first conduit including a passageway extending across the boundary of the container to its exterior to provide a flow path from the exterior of the container into the passageway;
a restriction formed in the first conduit between the at least one opening and the passageway;
a second conduit, at least a portion of the second conduit extending inside the first conduit adjacent the substantially closed end of the first conduit and in fluid communication with the first conduit, the second conduit extending away from the substantially closed end of the first conduit, the second conduit including a channel extending across the boundary of the container in fluid communication with the first line;

the pressurized fluid source being connected to the passageway to provide pressurized fluid to the first conduit;

wherein pressurized fluid flowing through the first conduit into the container passing the restriction, creating a reduced pressure adjacent the at least one opening to draw abrasive particles from the interior of the container into the first conduit, abrasive particles being entrained in the pressurized fluid flowing in the first conduit toward the substantially closed end, an amount of the particle-laden pressurized fluid flowing through the at least one apertures to the interior of the container, the remaining portion of the particle-laden pressurized fluid flowing past the substantially closed end of the first conduit and into the second conduit and then the channel to exit the container, and wherein the body includes a switch capable of activating the dental apparatus in one position and purging the dental apparatus in a second position.

25. A dental instrument comprising:

a body having a securing device for securing the body to a dental unit, the body directly attached an enclosed container, the enclosed container having a removable portion for holding abrasive particles, the body having a conduit extending inside the container and in fluid communication with the interior of the container, the conduit including a passageway extending across the boundary of the container to its exterior at a first location to provide a flow path from the exterior of the container into the passageway, the conduit including a channel extending across the boundary of the container to its exterior at a second location to provide a flow path from the channel to the exterior of the container, the conduit generally extending within the container from the first location of the container toward the second location of the container, the conduit including at least one opening to provide fluid communication from the interior of the container into the conduit, at least one aperture disposed between the at least one opening and the second location of the container in fluid communication with the interior of the container;

a restriction formed in the conduit between the at least one opening and the passageway;

a source of pressurized fluid being connected to the passageway to provide pressurized fluid to the conduit;

wherein pressurized fluid flowing through the conduit into the container passing the restriction, creating a reduced pressure adjacent the at least one opening to draw abrasive particles from the interior of the container into the conduit, abrasive particles being entrained in the pressurized fluid flowing in the conduit toward the at least one apertures, an amount of the particle-laden pressurized fluid flowing through the at least one apertures to the interior of the container, the remaining portion of the particle-laden pressurized fluid flowing past the at least one apertures of the conduit and then the channel to exit the container, and wherein the body includes a switch capable of activating the dental instrument in one position and purging the dental instrument in a second position.

* * * * *